(12) United States Patent
Van Groningen et al.

(10) Patent No.: US 9,220,866 B2
(45) Date of Patent: Dec. 29, 2015

(54) PACKAGE WITH CATHETER

(75) Inventors: David Van Groningen, Doetinchem (NL); Ad Van Velthoven, Beusichem (NL)

(73) Assignee: Curan Medical B.V., Doetinchem (NL)

( * ) Notice: Subject to any disclaimer, the term of this patent is extended or adjusted under 35 U.S.C. 154(b) by 233 days.

(21) Appl. No.: 13/883,568

(22) PCT Filed: Nov. 2, 2011

(86) PCT No.: PCT/NL2011/050743
§ 371 (c)(1),
(2), (4) Date: Jul. 5, 2013

(87) PCT Pub. No.: WO2012/060699
PCT Pub. Date: May 10, 2012

(65) Prior Publication Data
US 2013/0292286 A1    Nov. 7, 2013

(30) Foreign Application Priority Data

Nov. 4, 2010  (EP) .................................... 10189987
Apr. 29, 2011 (EP) .................................... 11164222

(51) Int. Cl.
*B65D 83/10*   (2006.01)
*B65D 81/24*   (2006.01)
*A61M 5/00*    (2006.01)
*A61M 25/00*   (2006.01)
*A61M 25/01*   (2006.01)

(52) U.S. Cl.
CPC .......... *A61M 25/002* (2013.01); *A61M 25/0111* (2013.01); *A61M 25/0017* (2013.01); *A61M 2025/0062* (2013.01)

(58) Field of Classification Search
CPC ... A61L 2/26; A61L 2202/182; A61M 5/001; A61M 5/002; A61M 25/002; A61M 25/0017; A61M 2025/0062
USPC ......... 206/363–365, 210, 438, 571, 221, 222; 604/172, 265, 544
See application file for complete search history.

(56) References Cited

U.S. PATENT DOCUMENTS

| | | | | |
|---|---|---|---|---|
| 3,114,455 A | * | 12/1963 | Stagg et al. | .................... 206/366 |
| 3,149,717 A | * | 9/1964 | Castelli | ......................... 206/365 |
| 3,229,813 A | | 1/1966 | Crowe, Jr. et al. | |
| 3,861,395 A | | 1/1975 | Taniguchi | |

(Continued)

FOREIGN PATENT DOCUMENTS

WO    03/008028 A2    1/2003

*Primary Examiner* — Chun Cheung
(74) *Attorney, Agent, or Firm* — Jordan IP Law, LLC; Todd A. Vaughn

(57) ABSTRACT

Package for a catheter, with a catheter having catheter tube with a distal end and a proximal end, the proximal end being provided with a catheter connector. A main body is provided for holding the catheter, and a cap for closing off the main body. A gel container is positioned inside the main body, the gel container being provided with a cavity for holding an amount of gel-like lubricating agent. The gel container comprises a first opening at a distal end, and a second opening at a proximal end. The catheter tube is disposed through the first opening and second opening when stored in the package. The main body is made of a rigid material to allow easy and reliable storage.

13 Claims, 3 Drawing Sheets

(56) References Cited

U.S. PATENT DOCUMENTS

| | | |
|---|---|---|
| 3,967,728 A | 7/1976 | Gordon et al. |
| 4,811,847 A | 3/1989 | Reif et al. |
| 6,578,709 B1 * | 6/2003 | Kavanagh et al. ............ 206/364 |
| 6,602,244 B2 * | 8/2003 | Kavanagh et al. ............ 604/544 |
| 6,634,498 B2 * | 10/2003 | Kayerød et al. ............... 206/364 |
| 8,579,115 B2 * | 11/2013 | Murphy et al. ................ 206/364 |
| 2006/0263404 A1 * | 11/2006 | Nielsen et al. ................ 424/422 |
| 2008/0183181 A1 | 7/2008 | Treacy et al. |

* cited by examiner

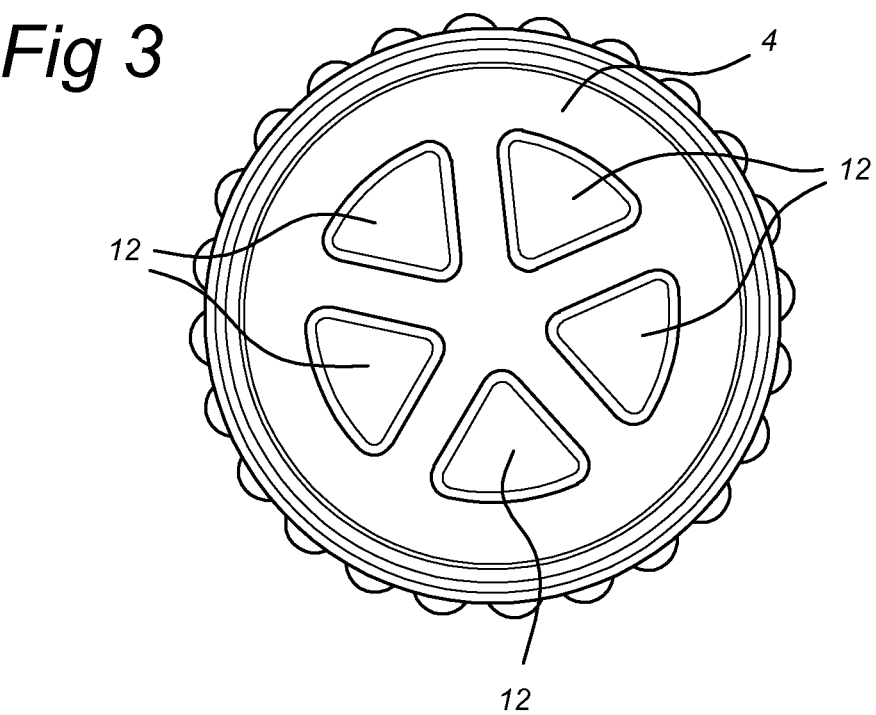

PACKAGE WITH CATHETER

CROSS-REFERENCE TO RELATED APPLICATIONS

The present application is a National Stage Application of PCT International Application No. PCT/NL2011/050743 (filed on Nov. 2, 2011), under 35 U.S.C. §371, which claims priority to European Patent Application Nos. 10189987.0 (filed on Nov. 4, 2010) and 11164222.9 (filed on Apr. 29, 2010), which are each hereby incorporated by reference in their respective entireties.

TECHNICAL FIELD

The present invention relates to a package with a catheter, e.g., a urethral catheter, which can be used for (intermittent) self-catheterization by a patient.

BACKGROUND

International patent publication WO03/008028 discloses a lubrication and gripping device for a urinary catheter package. The cap 30 closing off the package is at the side where the distal (tip) end of the catheter is positioned inside the package, and a supply of lubricant is positioned in the package just in front of the cap. The distal end of the catheter (tip part with openings) is exiting the package first, the catheter part with connector remains inside the flexible package. A holder 20 is provided with dedicated shape and material as a gripping device.

U.S. Pat. No. 3,861,395 discloses an automated catheter, and more in particular a catheter assembly within a protective removable envelope. A tube of a catheter is pulled through a body with a longitudinal bore for lubrication of the catheter.

U.S. Pat. No. 4,811,847 discloses a urinary catheter package having a rectangular tray with an open top, to which a peel back cover is bonded.

International patent publication WO00/47494 discloses a storage package with a catheter. The catheter is provided with a coated surface, which exhibits a reduced friction when wetted with a wetting liquid. The wetting liquid is provided in the storage package, and thus contacts the coated surface during the entire shelf live.

British patent application GB-A-2 319 507 discloses a packaged catheter with a lubricant activating liquid. In the package, which comprises the catheter, also a container with a liquid (water) is provided. Prior to actual use, the container may be opened such that the liquid can activate the coating on the catheter.

SUMMARY

The present invention seeks to provide an improved package for a (urethral) catheter, suitable for everyday use by a patient.

In accordance with the present invention, a package is provided as defined in claim 1. The rigid material is a material retaining its form under normal conditions, allowing to store the package with contents without a risk of deforming the contents of the package (as opposed to many prior art packages made of a foil like material). This also results in a package which is easy and safe to carry on a person, e.g. in a purse, bag or pocket, without a risk of lubricant leaking from the package. The material is e.g., a hard plastic material, such as a thermoplastic material (e.g., polycarbonate, PP, PE, PMMA) or a thermosetting material.

In a further embodiment, the main body is a closed off tube like element with an opening, the opening being closeable by the cap. In the present invention embodiment, the catheter is taken out from the package with the proximal end (connector) first, the catheter tip is taken out of the package as last.

In an even further embodiment the first opening diameter corresponds to a catheter diameter, and the second opening diameter is larger than the catheter diameter. The catheter is e.g. a urethral catheter, which may be used by the patient or a physician. This embodiment allows an equal and easy spread of the lubricating agent when opening the package and taking out the catheter (connector first), while having an easy to use and easy to store package. This makes the package according to the present invention suitable for intermittent self-catheterization.

In a further embodiment, the main body comprises a first part for receiving the cap, a second part for holding the gel container and a third part for holding a distal end of the catheter, in which the first part has an inner diameter which is less than an inner diameter of the second part, and the third part has an inner diameter which is less than the inner diameter of the second part. This allows to sufficiently seal off the package allowing it to be carried by a person before actual use.

The third part of the main body is arranged to hold the catheter tube in a space which is shorter than the length of the catheter tube. This variant would allow packaging of longer catheters, e.g., urethral catheters for men.

In an even further embodiment, the gel container comprises locking members extending beyond the inner diameter of the first part. This allows to lock the gel container in place inside the package in a simple and reliable manner.

The gel container comprises an inner sealing member (e.g., in the form of a ring) at the second opening, which in co-operation with the catheter (e.g., the connector part of the catheter) seals off the gel container. In a further variant, the catheter may comprise a closing member (e.g., as part of the connector) for sealing of the second opening of the gel container when positioned in the main body. This sealing member aids in preventing lubricating agent from escaping from the package before actual use of the catheter.

In a further embodiment, the outside dimensions of the package are congruent with the catheter. In other words, a first part of the package (where the connector is located) has an outside diameter smaller than an outside diameter of a second part (where the catheter tube is located). By following the shape of the catheter, a package may be provided with minimal dimensions, making it easy to carry and to store.

In an even further embodiment, the length of the package corresponds to the length of the catheter. This again makes possible a package with minimal dimensions, and allows quick identification of the catheter present in the package.

The lubricating agent comprises a gel in a further embodiment, allowing easy assembly of the package.

In order to make the catheter suitable for application by the major part of patients, in a further embodiment, the catheter is made of a material without softening agent, e.g., PVC with a nelaton tip.

In a further embodiment, the cap is made of a transparent material. This allows to have codes on the catheter (or on the catheter connector) to be visible while the package is still closed off. The codes may be dimension codes, application codes, etc.

The cap is provided with one or more openings in a further embodiment, and optionally with a filter element (such as a paper filter). This allows to sterilize the package and its contents after assembly, by gas sterilization.

In a further aspect, the present invention relates to a method for sterilizing a package in accordance with any one of the present invention embodiments, comprising assembling the main body, gel container, catheter and cap, and sterilizing internal elements of the package by introducing a sterilizing gas through the one or more openings in the cap. This is a very efficient and cost-effective manner of sterilizing the package and its contents in a sufficient manner. It is noted that U.S. Pat. No. 3,967,728 discloses a package for a catheter having a sachet with lubricant which can be ruptured. The sachet is disposed close to a distal end of the catheter allowing to bring at least the distal part of the catheter in contact with the lubricant before actual use. This document furthermore discloses that parts of the package may be sterilized before assembly of the entire package. The present invention embodiment allows to sterilize the entire package and its contents after assembly.

DRAWINGS

The present invention will be discussed in more detail below, using a number of exemplary embodiments, with reference to the attached drawings, in which:

FIG. 3 illustrates a top view of an embodiment of a cap of the package of FIG. 1.

DESCRIPTION

The embodiments of the present invention aim to provide an easy to use and easy to carry solution for providing a medical device in the form of a catheter. As an example, the medical device is a urethral catheter allowing to empty the bladder of patient. The present invention embodiments provide for a package in which a urethral catheter 1 can be carried, which is ready for use when taken from the package. The urethral catheter 1 may be used for intermittent self-catheterization.

Figure 1:
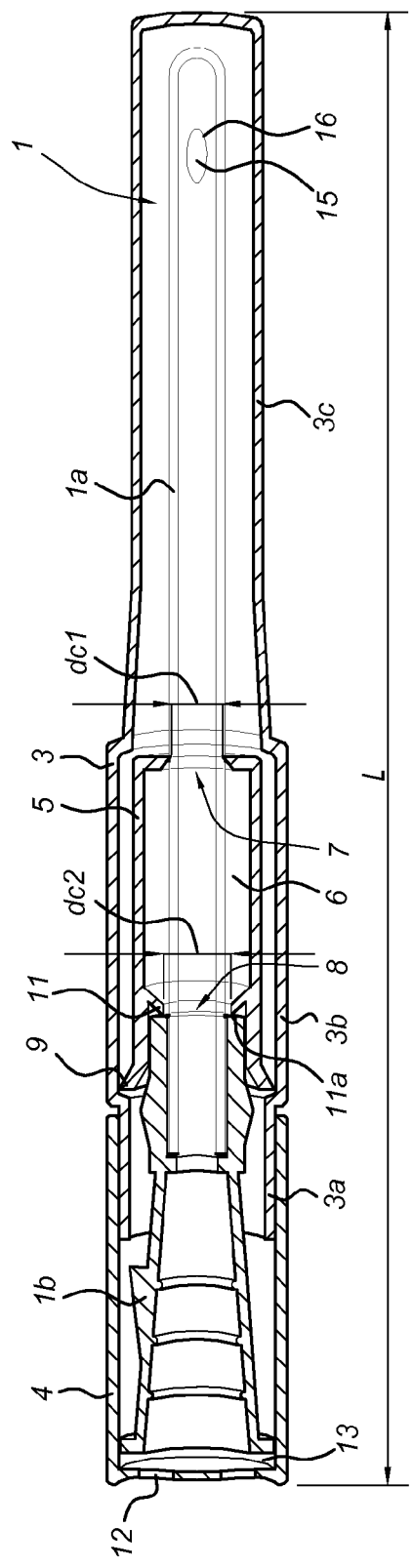
FIG. 1 illustrates a cross sectional view of a package in accordance with an embodiment of the present invention.

FIG. 1 illustrates a cross sectional view of an exemplary embodiment of the present invention, showing all elements is assembled state.

A main body 3 is provided which is closed off at a distal end, and which can be closed off at a proximal, open end using a cap 4. The cap 4 can be attached to the main body 3 using various attachment/locking methods, such as a screw thread, a bayonet closure or a clamping arrangement. In other words, the main body 3 is a closed off tube like element with an opening, the opening being closeable by the cap 4. The catheter 1 can then be taken out from the package 10 with its proximal end (connector) first, the catheter tip is taken out last.

The main body 3 is made of a rigid material, as opposed to a flexible, foil like material. The rigid material is a material retaining its form under normal conditions, allowing to store the package with contents without a risk of deforming the contents of the package. This also results in a package 10 which is easy and safe to carry on a person, e.g. in a purse, bag or pocket, without a risk of lubricant leaking from the package. The material is e.g., hard plastic material, such as a thermoplastic material (e.g. polycarbonate, PP, PE, PMMA) or a thermosetting material.

Figure 2A:
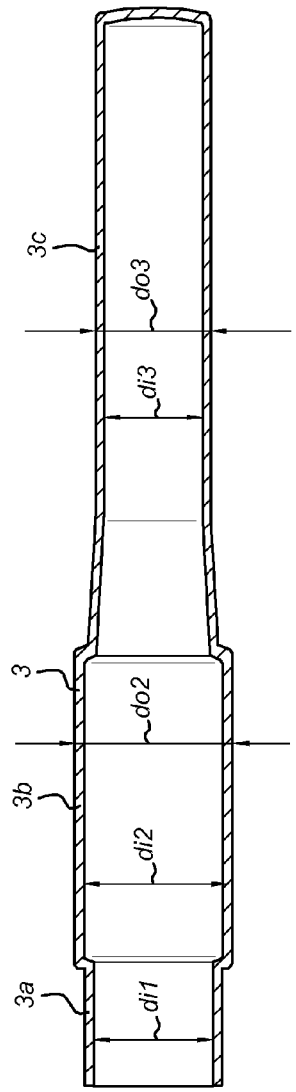
FIG. 2a illustrates a cross sectional view of an embodiment of a main body of the package of FIG. 1.

FIG. 2a illustrates a cross sectional view of the main body 3, which is divided in a first part 3a, second part 3b and third part 3c, which have a first internal diameter di1, di2 and di3, respectively. The first part 3a is arranged for receiving the cap 4, the second part 3b for holding a gel container 5 and the third part 3c for holding the catheter tube 1a of the catheter 1. In the embodiment shown, the first part 3a has an inner diameter di1 which is less than an inner diameter di2 of the second part 3b, and the third part 3c has an inner diameter di3 which is less than the inner diameter di2 of the second part 3b.

The cap 4 may have a dimension which allows the cap 4 to cover the outside of the first part 3a entirely, thus providing a pen-like appearance for the package. In an embodiment, the cap 4 is made of a transparent material, which allows inspection of the connector 1b of the catheter 1 (which e.g. shows size or other markings on the connector 1b).

As illustrated in the embodiments of FIG. 1 and FIG. 2a, the outer diameter of the third part 3c may have a transition part from the second part 3b. The outside dimensions of the package are congruent with the general form of the catheter 1, or follows the general dimensions of the catheter 1, i.e., the package 10 is a long, pen shaped package. In more general terms, a first part of the package 10 has an outside diameter smaller than an outside diameter of a second part (i.e., the outer diameter do3 of the third part 3c of the main body 3 is smaller than the outside diameter do2 of the second part 3b, as illustrated in FIG. 2a).

Figure 2B:
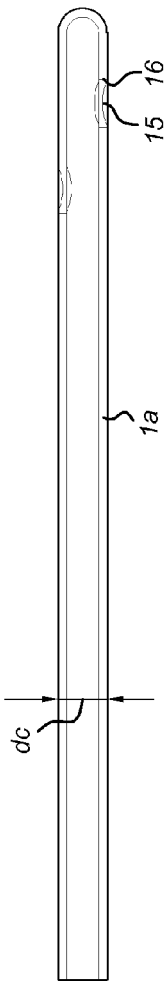
FIG. 2b illustrates a cross sectional view of an embodiment of a catheter of the package of FIG. 1.

A urethral catheter 1 is illustrated in the view of FIG. 2b. The urethral catheter 1 is stored in the main body 3, and comprises a distal end in the form of a catheter tube 1a provided with a rounded end and one or more discharge openings 15. The openings 15 are provided with rounded and or polished rims 16, such that the entry of the urethral catheter tube 1a in to the urethral tract is as comfortable as possible for the patient. At a proximal end the catheter 1 is provided with a catheter connector 1b, which may be used to attach the catheter 1 to a collection bag or other collection device. The dimensions of the package 10 (or more specific the internal dimensions of the main body 3 and cap 4) are adapted to allow storage of the entire catheter 1 (which may have varying dimensions). In the embodiment shown, the catheter 1 is about 10-15 cm, which makes this catheter 1 especially suited for use with female patients.

In an embodiment, the length L of the package (see FIG. 1) corresponds to the length of the catheter 1 (i.e. is slightly larger than the catheter 1 so that the package surrounds the entire catheter 1).

The urethral catheter 1 is made of a plastic material without any softening agent in a specific embodiment, in order to prevent possible sensitivity issues with the patient. The material may e.g. be a PVC type of material, and the catheter tube 1a may be provided with a nelaton tip.

Figure 2C:
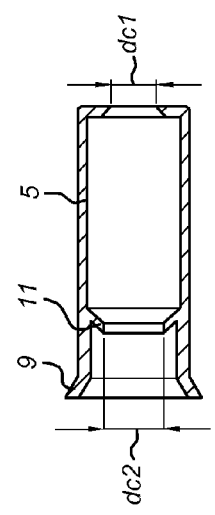
FIG. 2c illustrates a cross sectional view of an embodiment of a gel container of the package of FIG. 1.

Furthermore, a gel container 5 is provided which is positioned in a second part 3b of the main body 3 as shown in the cross sectional view of FIG. 1. In FIG. 2c, the gel container 5 is shown as single element. The gel container 5 is provided with a cavity 6, in which an amount of a gel-like lubricant agent is stored. The gel container 5 comprises a first opening 7 at a distal end, and a second opening 8 at a proximal end, the first opening diameter dc1 corresponding in general to a diameter dc of the catheter 1, and the second opening dc2 diameter being larger than the catheter diameter dc. This allows to provide a layer of the gel-like lubricant on the outside surface of the entire catheter 1 when taking the catheter out of the package, making the catheter 1 instantaneously ready for use. The catheter tube 1a is disposed through the first opening 7 and second opening 8 when stored in the package 10. The first opening 7 may be provided as a skewed surface in the material of the gel container 5, with a diameter dc1 smaller than the outer diameter dc of the catheter tube 1b, the flexible material then providing a good sealing of the first opening 7 against the outer wall of the catheter tube 1b.

The lubricating agent comprises a gel-like material in an embodiment of the present invention. In further embodiments, additional components may be included in the lubricating agent, such as compositions having a medicinal function.

The gel container 5 is held in position in the main body 3 by matching the dimensions of the gel container 5 to the inner diameter di2 of the second part 3b. The gel container 5 is provided with one or more locking members 9, which extend beyond the inner diameter di1 of the first part 3a. During manufacturing, the gel container 5 can be forced into position in the second part 3b of the main body 3, and the locking members 9 assure a proper fixation of the gel container 5. The locking members are e.g. extensions of the material of the gel container 5, or a ring like extension of flexible material. The gel container 5 is e.g. made of a soft material, such as silicone.

In the embodiment illustrated in FIG. 1, the gel container 5 comprises an inner sealing member 11 at the second opening 8, which in co-operation with the catheter 1 (e.g., using a properly shaped end part 11a of the connector 1b) seals off the gel container 4. Also, the inner sealing member 11 provides a constant thickness film on the outer surface of the catheter tube 1b when the catheter 1 is taken out of the package.

In an alternative embodiment, the catheter 1 comprises a closing member, e.g., as part of the connector 1b, for sealing off the second opening 8 of the gel container 4 when the catheter 1 is positioned in the main body 3.

In a further embodiment, the third part 3c of the main body 3 is arranged to hold the catheter tube 1b of the catheter 1 in a space which is shorter than the length of the catheter tube 1b, e.g., in a folded or coiled up manner. This would also allow use of the present invention package embodiments for longer urethral catheters, e.g., intended for use by male patients.

In order to allow the package and catheter 1 to be used by patients themselves, the catheter 1 is sterilized when assembling the package with catheter 1. In a further aspect of the present invention, the cap 4 of the package is provided with one or more openings 12. These openings 12 are sealed off with a filter element 13 (as illustrated in the cross sectional view of FIG. 1), e.g., in the form of a paper element. After assembling the main body, gel container, catheter and cap, the internal elements of the package (i.e., the inner lumen of the main body 3 and catheter 1) by introducing (e.g., injecting) a sterilizing gas through the one or more openings in the cap 4.

The present invention embodiments have been described above with reference to a number of exemplary embodiments as shown in the drawings. Modifications and alternative implementations of some parts or elements are possible, and are included in the scope of protection as defined in the appended claims.

What is claimed is:

1. A package for a catheter, comprising:
   a catheter having a catheter tube with a distal end and a proximal end, the proximal end being provided with a catheter connector;
   a main body for holding the catheter, wherein the main body is made of a rigid material and includes a first part, a second part, and a third part for holding the distal end of the catheter tube, wherein the first part has an inner diameter which is less than an inner diameter of the second part, and the third part has an inner diameter which is less than the inner diameter of the second part;
   a cap for closing off the main body and which is received by the first part, wherein the main body and the cap enclose the catheter tube entirely; and
   a gel container positioned inside the main body and held by the second part, the gel container being provided with a cavity for holding an amount of gel-like lubricating agent, and comprising a first opening at a distal end and which has a first opening diameter that corresponds to a catheter diameter, and a second opening at a proximal end and which has a second opening diameter that is greater than the catheter diameter, the catheter tube being disposed through the first opening and second opening when stored in the package.

2. The package of claim 1, wherein the main body is a closed off tube like element with an opening, the opening being closeable by the cap.

3. The package of claim 1, wherein the third part is arranged to hold the catheter tube in a space having a length which is less than the length of the catheter tube.

4. The package of claim 1, wherein the gel container comprises an inner sealing member at the second opening, which in co-operation with the catheter seals off the gel container.

5. The package of claim 1, wherein the package has outside dimensions that are congruent with the catheter.

6. The package of claim 1, wherein the package has a length that corresponds to a length of the catheter.

7. The package of claim 1, wherein the lubricating agent comprises a gel.

8. The package of claim 1, wherein the catheter is composed of a material without softening agent.

9. The package of claim 1, wherein the cap is composed of a transparent material.

10. The package of claim 1, wherein the cap is provided with one or more openings.

11. The package of claim 1, wherein the cap is provided with a plurality of openings.

12. A method of sterilization, the method comprises:
   providing a package that includes a catheter having a catheter tube with a distal end and a proximal end, the proximal end being provided with a catheter connector; a main body for holding the catheter, wherein the main body is made of a rigid material and includes a first part, a second part, and a third part for holding the distal end of the catheter tube, wherein the first part has an inner diameter which is less than an inner diameter of the second part, and the third part has an inner diameter which is less than the inner diameter of the second part; a cap for closing off the main body and which is received by the first part, wherein the main body and the cap enclose the catheter tube entirely; a gel container positioned inside the main body and held by the second part, the gel container being provided with a cavity for holding an amount of gel-like lubricating agent, and comprising a first opening at a distal end and which has a first opening diameter that corresponds to a catheter diameter, and a second opening at a proximal end and which has a second opening diameter that is greater than the catheter diameter, the catheter tube being disposed through the first opening and second opening when stored in the package;
   assembling the main body, the gel container, the catheter and the cap; and
   sterilizing internal elements of the package by introducing a sterilizing gas through one or more openings in the cap.

13. A package for a catheter, comprising:
a catheter having a catheter tube with a distal end and a proximal end, the proximal end being provided with a catheter connector;
a main body for holding the catheter, wherein the main body is made of a rigid material and includes a first part, a second part, and a third part for holding the distal end of the catheter tube, wherein the first part has an inner diameter which is less than an inner diameter of the second part, and the third part has an inner diameter which is less than the inner diameter of the second part;
a cap for closing off the main body and which is received by the first part, wherein the main body and the cap enclose the catheter tube entirely; and
a gel container positioned inside the main body and held by the second part, the gel container being provided with locking members extending beyond the inner diameter of the first part, and a cavity for holding an amount of gel-like lubricating agent, and comprising a first opening at a distal end and which has a first opening diameter that corresponds to a catheter diameter, and a second opening at a proximal end and which has a second opening diameter that is greater than the catheter diameter, the catheter tube being disposed through the first opening and second opening when stored in the package.

\* \* \* \* \*